United States Patent [19]
Chen et al.

[11] Patent Number: 5,448,178
[45] Date of Patent: Sep. 5, 1995

[54] TRANSIENT TECHNIQUE TO DETERMINE SOLUTION RESISTANCE FOR SIMPLE AND ACCURATE CORROSION RATE MEASUREMENTS

[75] Inventors: Tzu-Yu Chen; Frank F.-Y. Lu, both of Naperville; Martin R. Godfrey, Elburn, all of Ill.

[73] Assignee: Nalco Chemical Company, Naperville, Ill.

[21] Appl. No.: 148,126

[22] Filed: Nov. 5, 1993

[51] Int. Cl.$^6$ .................. G01N 17/02; G01N 27/26
[52] U.S. Cl. ............................... 324/700; 324/71.2; 204/153.1; 204/404
[58] Field of Search .............. 324/71.1, 71.2, 700, 324/439; 73/86; 204/153.11, 40 M

[56] References Cited

U.S. PATENT DOCUMENTS

| | | | |
|---|---|---|---|
| 4,095,176 | 6/1978 | Maes et al. | 204/153.11 |
| 4,238,298 | 12/1980 | Tsuru et al. | 324/71.2 X |
| 4,831,324 | 5/1989 | Asakura et al. | 324/71.2 X |
| 5,139,627 | 8/1992 | Eden et al. | 204/153.11 |

FOREIGN PATENT DOCUMENTS

| | | | |
|---|---|---|---|
| 0117142 | 6/1985 | Japan | 324/700 |
| 4342520 | 12/1987 | U.S.S.R. | |
| 4398225 | 1/1988 | U.S.S.R. | |

Primary Examiner—Maura K. Regan
Assistant Examiner—Diep Do
Attorney, Agent, or Firm—Robert A. Miller; James J. Drake

[57] ABSTRACT

An apparatus and a method are provided for determining solution resistance and corrosion rate of a metal surface contained in a solution such as an electrode. The signal is applied to the metal surface of interest and the current response is monitored from the applied signal. A peak detector is provided for detecting the peak of the current response. From the peak, the resistance of the solution is ascertained. Following independent determination of the solution resistance, polarization resistance of the metal surface in the solution may be determined. The corrosion rate of the metal surface may be calculated from the polarization resistance.

10 Claims, 5 Drawing Sheets

TRANSIENT TECHNIQUE TO DETERMINE SOLUTION RESISTANCE FOR SIMPLE AND ACCURATE CORROSION RATE MEASUREMENTS

BACKGROUND OF THE INVENTION

The present invention generally relates to an apparatus and a method for determining corrosion rate. More specifically, the invention relates to a transient technique utilizing a potential step or pulse and applying that signal to a metal/solution interface in order to determine solution resistance. A measurement of corrosion rate can be ascertained from at least the solution resistance.

A number of methods are known for ascertaining the rate of corrosion. Typically, electrochemical techniques for corrosion measurements are based on the Stearn-Geary equation. This equation is generally known as follows:

$$I_{corr} = \frac{1}{2.303} \frac{B_a \cdot B_c}{B_a + B_c} \frac{1}{R_p}$$

wherein
- $I_{corr}$ = corrosion rate (current density),
- $B_a$ = anodic Tafel slope (mV),
- $B_c$ = cathodic Tafel slope (mV), and
- $R_p$ = polarization resistance (Ohms.cm$^2$)

From this equation, the corrosion rate can be determined by measuring the polarization resistance $R_p$ for known values of $B_a$ and $B_c$. The corrosion rate in current density, $I_{corr}$, can further be converted to corrosion rates in other units, such as mils per year (mpy) and millimeters per year (mm/yr.), based on Faraday's law.

In a conventional linear polarization technique, a small potential excitation is applied across a corroding metal surface at a very slow scan rate to quantify the total resistance as the sum of solution resistance ($R_s$) and polarization resistance ($R_p$). Therefore, linear polarization can be used for corrosion rate measurements when $R_s$ is very small compared to $R_p$ wherein $$R_s + R_p \approx R_p.$$

However, in many instances, $R_s$ is not negligible as compared to $R_p$. Therefore, $R_s$ must be determined in a separate experiment. That is, to accurately measure the corrosion rate, a conventional linear polarization technique cannot be implemented if $R_s$ is not negligible.

One known method for calculating solution resistance ($R_s$) is known as the "current interrupt" method. In this method, a small current $i_c$ is applied to an electrode for a short time period. At a later point in time, the current $i_c$ is interrupted. The potential difference between this electrode and a reference electrode is monitored before and after the current $i_c$ is interrupted. FIG. 7 illustrates the manner in which the solution resistance $R_s$ is estimated using this method by plotting the potential as it varies over time. That is, from the measurements, the solution resistance $R_s$ may be approximated or extrapolated by the equation:

$$\text{Estimated } R_s = \frac{E_s}{i_c}$$

The actual solution resistance is $E_R/i_c$ as indicated in FIG. 7. This current interrupt method, however, provides an approximation or extrapolation that can be very inaccurate for calculating solution resistance, $R_s$, especially when $R_s$ is large.

Another method for determining the solution resistance $R_s$ is known as the "AC impedance" technique or "Electrochemical Impedance Spectroscopy (EIS)." With this method, the actual solution resistance may be calculated from the equation:

$$R_s = \lim_{\text{freq.} \to \infty} \frac{\Delta E}{\Delta i}$$

wherein a small amplitude AC sinusoidal potential wave, $\Delta E$, at a very high frequency (freq.), typically 10 KHz, is applied to the metal surface in the solution to measure the current response, $\Delta i$.

The apparatus required, however, for performing calculation of the solution resistance using the AC impedance method (or Electrochemical Impedance Spectroscopy, EIS) is expensive and furthermore is not well-suited for long term field use due to its size and weight.

A need, therefore, exists for an improved method for determining solution resistance to provide simple and accurate corrosion rate measurements.

SUMMARY OF THE INVENTION

A method and an apparatus are provided for determining solution resistance of a solution in contact with a metal surface, such as a metal electrode. From the determination of solution resistance, corrosion rate of the metal surface may be derived.

To this end, in an embodiment, a method is provided for determining solution resistance of a solution having a metal surface therein. The method comprises the steps of applying a signal to the metal surface; monitoring the current response to the signal; providing a peak detector; applying the current response to the peak detector; determining the peak of the current response; and ascertaining the solution resistance of the solution from the peak.

In an embodiment, the signal applied to the metal surface is a small amplitude potential step.

In an embodiment, the metal surface in the solution is a metal electrode.

In an embodiment, the solution is boiler feed water or steam condensate having a low conductivity; or other low-conductivity aqueous or non-aqueous solutions; or when the value of the solution resistance is very close to that of the polarization resistance in high-conductivity solutions; or cooling water environments.

In an embodiment, the method further comprises the step of converting the current response to a voltage response before applying the same to the peak detector.

In an embodiment, a method is provided for determining corrosion rate of a metal surface in a solution. The method comprises the steps of determining, independently, solution resistance; determining the sum of the solution resistance and the polarization resistance of the metal surface in the solutions; and calculating the corrosion rate of the metal surface from the polarization resistance.

In an embodiment, the step of determining the solution resistance further comprises the steps of applying a transient potential signal to the surface; monitoring the current response to the signal; determining the peak of the current response; and ascertaining the solution resistance from the peak.

In an embodiment, the present invention further provides an apparatus for calculating corrosion rate of a metal surface in a solution. The apparatus comprises signal generating means for providing a potential signal to the metal surface. A peak detector determines the peak of the current response to the potential signal, and a calculating means determines solution resistance from the peak wherein the corrosion rate is derived from at least the solution resistance.

In an embodiment, the peak detector of the apparatus employs a resistor or a current-to-voltage converter providing a voltage signal to the peak detector.

In an embodiment, the calculating means of the apparatus determines polarization resistance before deriving the corrosion rate.

It is, therefore, an advantage of the present invention to provide a simple method and a simple apparatus for determining solution resistance.

Another advantage of the present invention is to provide a simple method and a simple apparatus for determining corrosion rate from at least the solution resistance.

A further advantage of the present invention is to provide a method and apparatus for accurately determining solution resistance.

Still further, an advantage of the present invention is to provide a method and an apparatus for accurately determining corrosion rate from at least the solution resistance.

Moreover, an advantage of the present invention is to provide an inexpensive apparatus and method for determining solution resistance and corrosion rate of a metal surface in a solution.

And, an advantage of the present invention is to provide a method and an apparatus implementing a peak detector for detecting the peak current in order to derive solution resistance therefrom by the equation:

$$R_s = \frac{E_a}{i_p}$$

where $E_a$ is the amplitude of the applied potential signal and $i_p$ is the peak of the current response.

A still further advantage of the present invention is to provide a method and an apparatus suitable for field use for determining solution resistance and corrosion rate.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention relates to a method and an apparatus for measuring corrosion rate. More specifically, the invention relates to a method and an apparatus for determining solution resistance. The method and the apparatus use a peak detector to determine the solution resistance at an interface of a corroding metal surface, such as a metal electrode, in aqueous or non-aqueous solutions.

Figure 1:
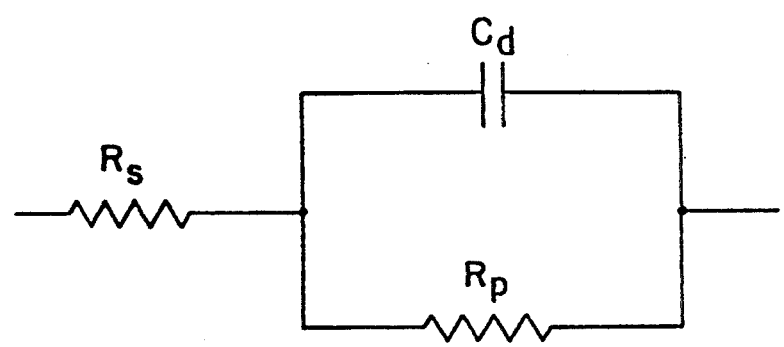
FIG. 1 illustrates an equivalent circuit representative of a corroding metal surface, such as a corroding electrode in a solution.

Referring now to FIG. 1, an equivalent circuit representing a metal surface subjected to corrosion is generally illustrated. A metal surface, such as an electrode, is generally subjected to corrosion when in a solution. Electrodes are typically used to measure corrosion rate. The apparatus and method of this invention is particularly well adapted to determine the corrosion rate of metals in contact with aqueous and non-aqueous low conductivity solutions. The invention is particularly useful in determining the corrosion rates of metals in contact with boiler feed water, steam condensate, industrial cooling waters, and other aqueous and non-aqueous solutions having a low conductivity. Although it will be apparent to those skilled in the art, corrosion rate measurements can be made in any low conductivity solution.

The equivalent circuit illustrated in FIG. 1 representative of a corroding metal surface includes a solution resistance $R_s$ in series with a parallel combination of a polarization resistance $R_p$ and a double layer capacitance $C_a$. Applying a high frequency AC signal to the circuit provides a substantially short circuit across the capacitor $C_a$ thereby providing an equivalent resistance equal to the solution resistance $R_s$. A low frequency AC or a DC signal, on the contrary, results in an open circuit substantially created across the capacitor $C_d$ and an equivalent total resistance $(R_s + R_p)$ equal to the sum of the solution resistance $R_s$ and the polarization resistance $R_p$ for the illustrated circuit of the corroding metal surface.

For solutions with a high conductivity and substantially no solution resistance, i.e. $R_s << R_p$, the total resistance is substantially equal to the polarization resistance $R_p$. However, many solutions such as boiler feed water and steam condensate, for example, have a high solution resistance $R_s$. When the solution resistance $R_s$ is substantial, it cannot be ignored. In a preferred embodiment of this invention, the value of the solution resistance is not negligible when compared to the polarization resistance.

For highly corrosive solutions such as dilute hydrochloric acid solutions the value of solution resistance may be higher or equivalent to that of the polarization resistance. In this case, the solution resistance cannot be ignored in the calculation of the corrosion rate because the solution resistance is a significant portion of the total resistance. Otherwise, significant error will be introduced.

Figure 2:
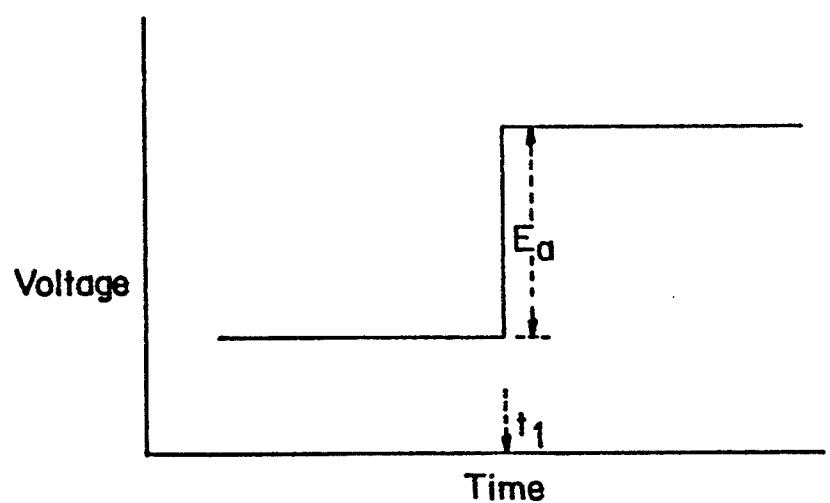
FIG. 2 illustrates a graph of a potential step to be applied to the corroding metal surface of FIG. 1.
Figure 3:
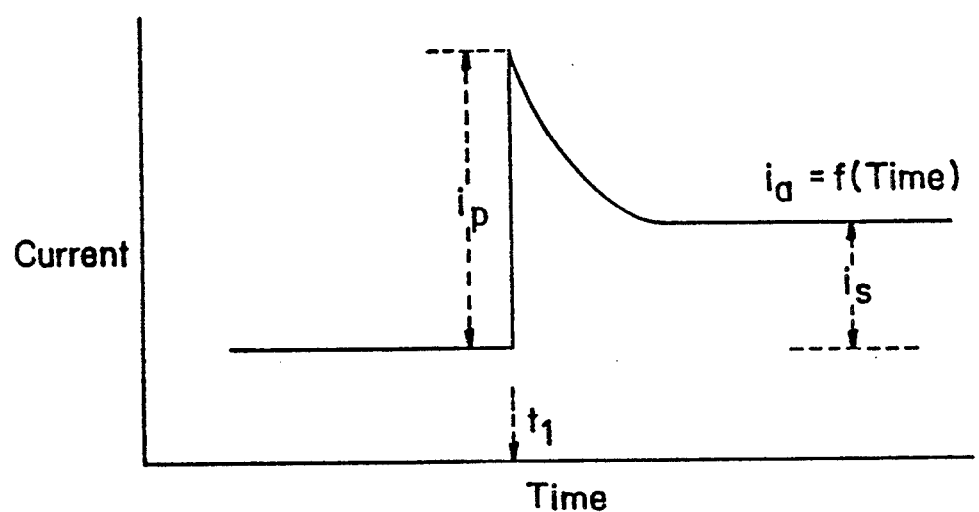
FIG. 3 illustrates a graph of the response of the current from the potential step applied as shown in FIG. 2.

FIGS. 2 and 3 illustrate application of a small amplitude potential step $E_a$, for example, $\pm 10$ mV or $\pm 20$ mV, to the equivalent circuit illustrated in FIG. 1. The small amplitude potential step may also be defined as the application of a pulse to the equivalent circuit. As previously discussed, the current substantially passes through the solution resistance $R_s$ and then the capacitor $C_d$ since the resistance of the capacitor to current flow is negligible or nearly zero (short circuit) for transient signals and high frequency AC signals. The current response $i_a$ from application of the potential step, such as $E_a$ illustrated in FIG. 2, is illustrated as a function of time as shown in FIG. 3 where $i_a = f(t)$. By measuring the magnitude of the maximum value of the current, $i_p$, the solution resistance $R_s$ may be calculated as follows:

$$R_s = \frac{E_a}{i_p}$$

To determine $R_s$, the maximum value of the current, $i_p$, must be determined.

Figure 4:
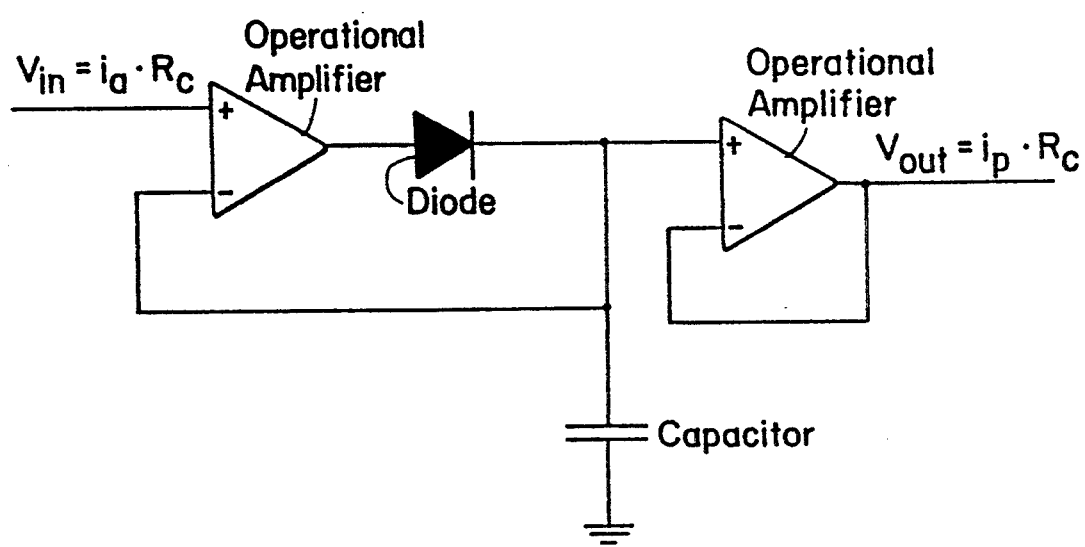
FIG. 4 illustrates an embodiment of a diagram of a typical peak detector for use in the method and apparatus of the present invention.

The present invention provides a simple and accurate method for calculating the maximum value of the current or the peak current $i_p$. To this end, a peak detector is provided as illustrated in FIG. 4. A current measuring resistor, $R_c$ (not shown) is implemented to convert a current signal $i_a$ at the input of the peak detector to a voltage signal $V_{in}$. Of course, other means for converting the current signal to a voltage signal may be implemented by the skilled artisan.

Figure 5:
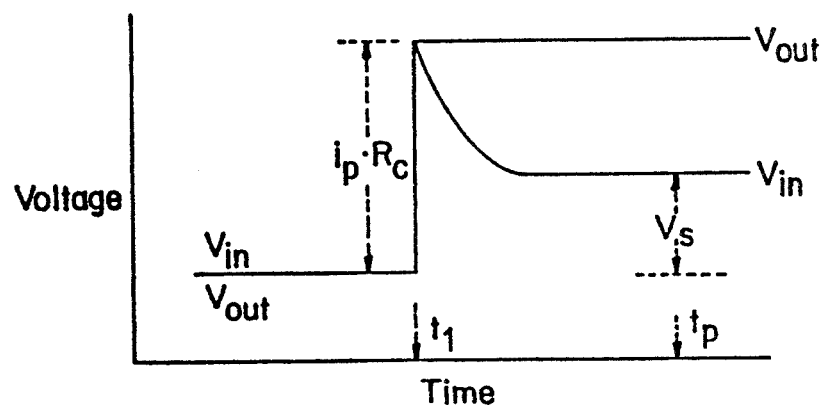
FIG. 5 illustrates a graph of the input ($V_{in}$) and output ($V_{out}$) of the peak detector of FIG. 4.

The peak detector is an analog device which continuously detects the variation of the signal with time and records the maximum value of the signal. That is, when using a current-measuring resistor, the maximum current is recorded in terms of voltage as illustrated in FIG. 5. The peak value can then be acquired from the peak detector at a pre-selected time interval $t_p$ as illustrated in FIG. 5 where $t_p$ is greater than $t_1$. The time $t_1$ is the time at which the potential signal is actually applied. Therefore, after calculating the peak current from the following equation:

$$i_p = \frac{V_{out}}{R_c}$$

the solution resistance can be calculated as follows:

$$R_s = \frac{E_a}{i_p} = \frac{E_a R_c}{V_{out}}$$

It should be understood that FIG. 4 illustrates a schematic diagram of a typical peak detector, but other peak detectors may be implemented by those skilled in the art to determine the peak current.

After ascertaining the solution resistance $R_s$, linear polarization may then be implemented to determine the total resistance $R_s + R_p$ at a slow potential scan rate such as 0.1 mV per second. Therefore, the polarization resistance $R_p$ can be determined by subtracting the solution resistance R, obtained by use of the peak detector from the total resistance calculated by the linear polarization technique, i.e. the total resistance equals the sum of the solution resistance $R_s$ and the polarization resistance $R_p$. Alternatively, the sum $(R_s + R_p)$ of the solution resistance $R_s$ and the polarization resistance $R_p$ may be determined by ascertaining the steady state value $i_s$ of the current response $i_a$ as follows:

$$R_s + R_p = \frac{E_a}{i_s} = \frac{E_a R_c}{V_s}$$

Figure 6:
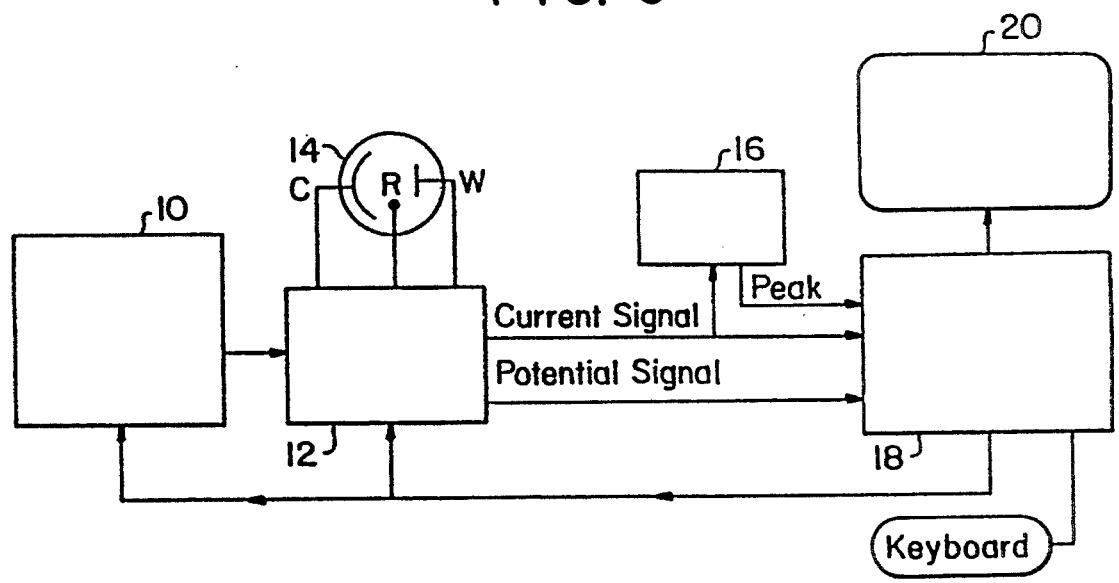
FIG. 6 illustrates a black box diagram of the components of the present invention for calculating corrosion rate.
Figure 7:
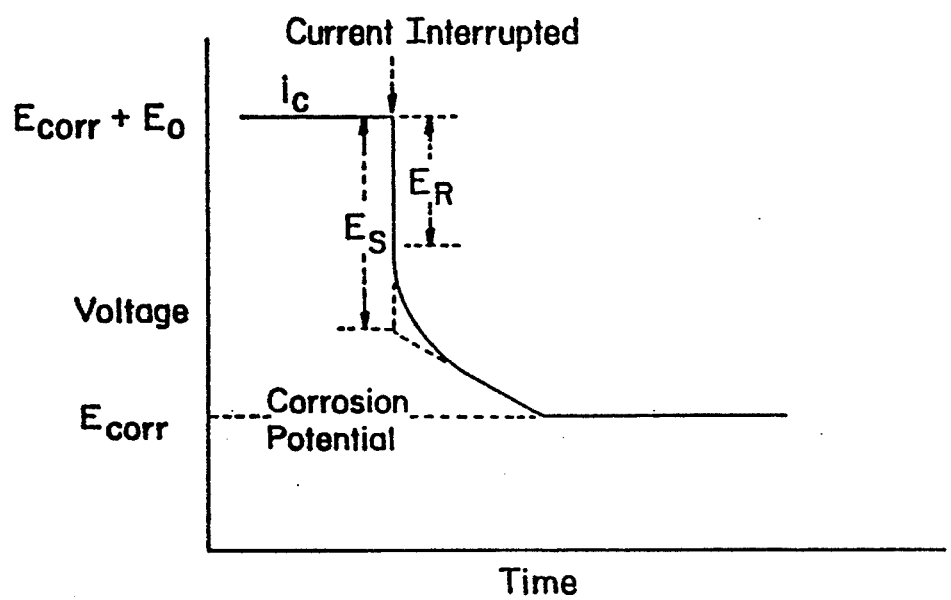
FIG. 7 illustrates a graph of potential response using a current interrupt method as is generally known from the prior art.

FIG. 6 generally illustrates the block diagram of the components for carrying out the steps of the method of the present invention. A signal generator 10 or a digital-to-analog converter provides a small potential signal to the electrochemical cell 14 through a potentiostat 12. We prefer to use a digital-to-analog converter to generate the potential signal. The potential signal is a potential step with an amplitude of $\pm 10$ mV, $\pm 20$ mV, or $\pm 30$ mV, we prefer to use a $+10$ mV step. The potential signal is small in amplitude and it is generally considered as nondestructive to the metal electrode on which the corrosion rate is being measured. The electrochemical cell consists of three electrodes including a counter electrode (C), a reference electrode (R) and a working electrode (W). We prefer to use three identical electrodes made of the metal on which the corrosion rate is to be determined in the electrochemical measurements. We commonly employ metal alloys used for water system piping such as mild steel or admiralty brass. However, a noble metal, such as platinum., can be used for the counter electrode. A silver/silver chloride electrode, a mercury/mercury chloride electrode or other commercially available reference electrodes could also be used as the reference electrode for the electrochemical cell. Alternatively, a two-electrode electrochemical system can be employed. In this case, the reference electrode terminal of the potentiostat is short-circuited with the counter electrode terminal of the potentiostat. Two identical metal electrodes on which the corrosion rate will be measured are then connected to the counter electrode terminal and the working electrode terminal of the potentiostat, respectively. Both the three-electrode and the two-electrode systems are commercially available as premanufactured probes with electrodes fashioned from the appropriate metal for insertion into industrial water piping systems, for example, probes under the trade name "Corrator."

The potential difference between the working and the reference electrodes and the response current of the electrochemical cell are monitored by a personal computer 18 equipped with analog/digital (A/D) and digital/analog (D/A) interfaces. The current response is also applied to a peak detector 16 for measuring the maximum value of the current response. It is not necessary to place the peak detector outside the potentiostat. We prefer to use circuitry custom fabricated for this purpose that includes a digital-to-analog converter, an analog-to-digital converter, a potentiostat, and a peak detector housed in a single chassis. The peak of the current response is then input to the personal computer 18 for calculating the solution resistance.

The polarization resistance $R_p$ may then be calculated by one of two methods. The steady state value of the current response after the application of the potential step may be measured and converted to a value for $R_s + R_p$ by the computer 18. We prefer this method to measure the total resistance ($R_s+R_p$). Alternately, the linear polarization technique in which a small amplitude (e.g. ±10 mV, ±20 mV, or ±30 mV we prefer ±10 mV) potential sweep is applied to the working electrode at a very slow potential scan rate, typically 0.1 mV per second can be used to measure ($R_s+R_p$). The polarization resistance can be determined by subtracting solution resistance $R_s$ (determined from the peak detector) from the total resistance ($R_s+R_p$) (determined from the application of a potential step or a potential sweep). The corrosion rate $I_{corr}$ can then be calculated from polarization resistance $R_p$ using the Stern-Geary equation previously set forth. It should also be noted that the potential sweep for the linear polarization experiment need not be continuous but can be approximated by a series of small potential steps, we prefer 2 mV steps, so long as the average scan rates are identical. With the personal computer the measurements can be fully automatic and the results can be provided to an output device 20, such as a video display, a printer, a data storage unit, or the like.

EXAMPLES

1. Dummy Cells

Figure 8:
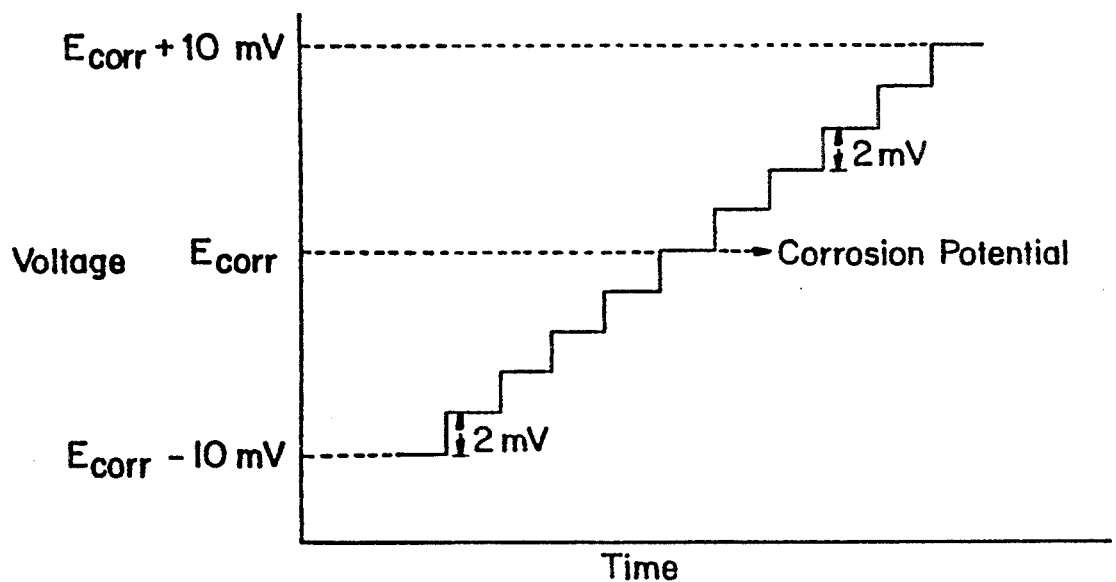
FIG. 8 illustrates a schematic diagram of the potential sep signal used in tests run using the apparatus of FIG. 6.
Figure 9:
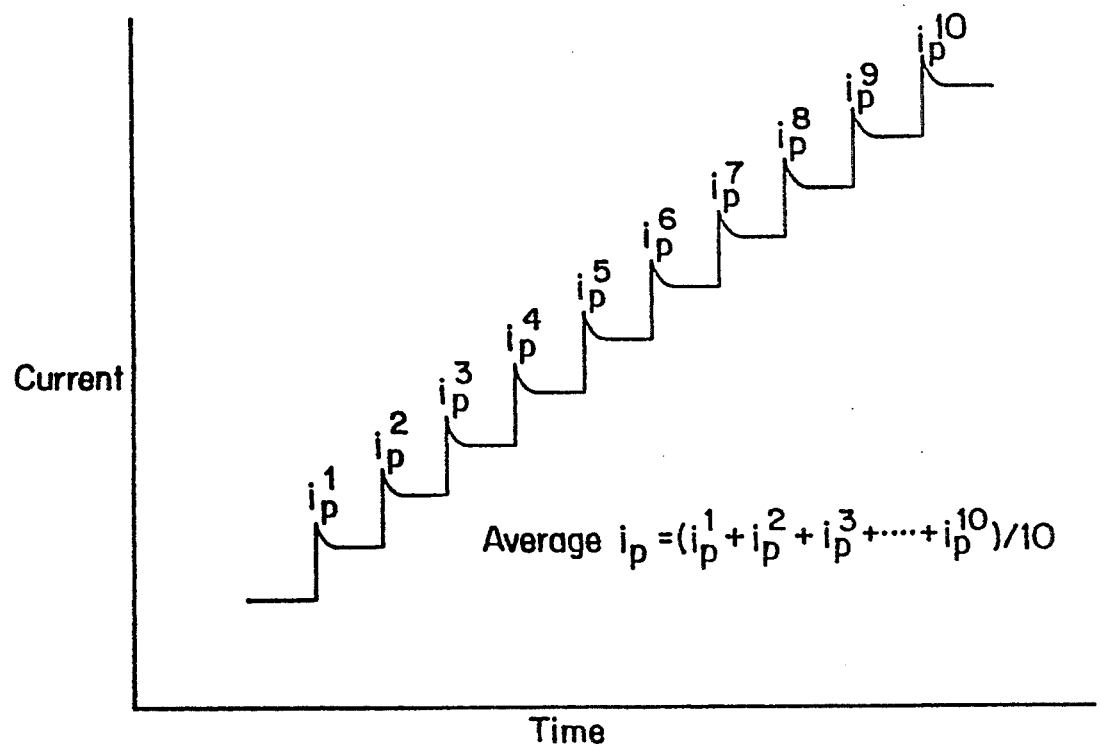
FIG. 9 illustrates the response current from the application of the potential step signal used in tests run using the apparatus of FIG. 6.
Figure 10:
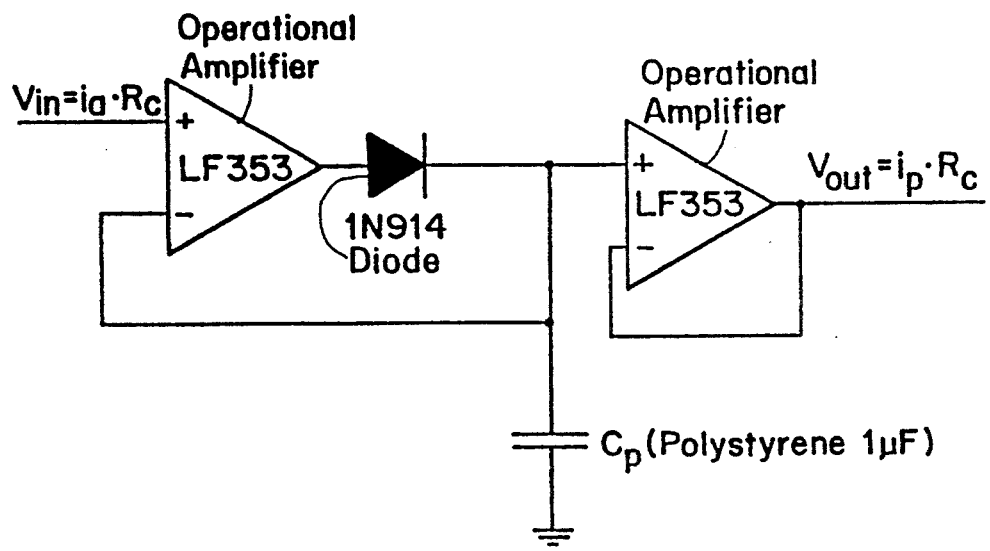
FIG. 10 illustrates a schematic diagram of a peak detector apparatus used as part of the corrosion monitor.

A prototype corrosion monitor including the components shown in FIG. 6 was constructed. The operating range of the monitor was determined with dummy cells, such as that shown in FIG. 1, made of various resistors and a 100 μF capacitor. A digital/analog card (part no. DAC 312, Analog Device) with a personal computer was employed to generate a potential sweep signal of ±10 mV in amplitude. The potential sweep for the linear polarization experiment was also produced by the digital/analog card by using 10 steps with each step being 2 mV in magnitude. The total measuring tide was 200 seconds for the 10-step potential signal and the measuring time for each 2 mV step was 20 seconds. Therefore the average potential sweep rate was 0.1 mV per second. FIG. 8 shows the schematic diagram of the potential step signal used in the tests, wherein $E_{corr}$, is the corrosion potential, i.e. the potential of the working electrode measured against the reference electrode before the application of the potential excitation. The schematic of response current from the application of such a signal is depicted in FIG. 9. A peak detector, FIG. 10, was constructed and was included in the corrosion monitor to detect the peak of the current and the solution resistance through a current-measuring resistor from the application of each 2 mV step. The peak values obtained from the 10 step potential signal were then averaged for the calculation of the solution resistance. The peak detector included a duo operational amplifier (part no. LF353, National Semiconductor), a diode (1N914) and a 1 μF polystyrene type capacitor. An analog/digital card (part No. CS5501, Crystal Semiconductor Corporation, Austin, Tex.) was used for data acquisition with a personal computer. The steady state value of each 2 mV step was recorded and at the end of the experiment the potential was plotted against the steady state current to calculate the total resistance as ($R_s+R_p$) as the slope of the potential versus current curve.

Data from these dummy cell experiments are given in Table 1 below.

TABLE 1

| DUMMY CELL EXPERIMENTS (Units: ohms) | | | | | | |
|---|---|---|---|---|---|---|
| Dummy Cell C = 100 μF | Measured Values | | | | | |
| | Test #1 | Test #2 | Test #3 | Test #4 | Test #5 | Average |
| $R_s$ = 10K | 8.1K | 9.4K | 9.6K | 9.5K | 9.6K | 9.24K |
| $R_p$ = 10K | 11.8K | 10.2K | 10.1K | 10.2K | 10.4K | 10.54K |
| $R_s$ = 10K | 9.6K | 9.6K | 9.7K | 9.4K | 9.5K | 9.56K |
| $R_p$ = 100K | 89.7K | 91.8K | 91.7K | 91.6K | 91.5K | 91.26K |
| $R_s$ = 10K | 9.6K | 9.0K | 9.7K | 9.7K | 9.7K | 9.54K |
| $R_p$ = 479K | 474.6K | 483.3K | 482.9K | 480.6K | 483.7K | 481.02K |
| $R_s$ = 22K | 20.1K | 19.8K | 19.3K | 19.5K | 20.1K | 19.76K |
| $R_p$ = 479K | 482.3K | 470.4K | 474.0K | 473.9K | 479.7K | 476.06K |
| $R_s$ = 56K | 0.0K | 0.0K | 0.0K | 48.4K | 0.0K | 9.68K |
| $R_p$ = 479K | 535.0K | 527.8K | 418.4K | 483.0K | 425.2K | 477.88K |

Good agreement was observed in $R_s$ and $R_p$ between the measured and the actual values except for $R_s$=56K ohms and $R_p$=479K ohms. In this case, significant errors occurred in the solution resistance measured by the corrosion monitor. This was believed to be caused by the small excitation step (2 mV) used in the potential signal for measuring the solution resistance and/or the resolution limitations of the A/D and D/A cards. Modifications of the corrosion monitor to improve its performance are described in a later section.

2. Simulated Boiler Condensate Environments The corrosion monitor was also evaluated in a simulated boiler condensate environment. A corrosion probe was made by embedding three mild steel wires in an epoxy resin leaving a 2 cm long section exposed in the test water. The diameter of the wires was 1 mm and the exposure area of the electrode was approximately 0.63 $cm^2$. The electrodes were used as the counter electrode, the reference electrode, and the working electrode, respectively. The corrosion probe was immersed in deaerated deionized water contained in a 1000 ml glass cell at room temperature. The conductivity of the test water was approximately 0.2 μS/cm at the beginning of the experiment. To simulate boiler condensate conditions oxygen was removed from the solution by parging with argon gas for two hours before the experiment. The corrosion probe was then immersed into the test water. Argon gas was continuously purged into the water during the course of the experiment.

Performance of the corrosion monitor using the peak detector was evaluated by comparison to two other electrochemical techniques. Simple linear polarization (LP) measurements were carried out using a +10 mV potential sweep at a potential scan rate of 0.1 mV per second with an EG&G Princeton Applied Research Model 273 Potentiostat. As mentioned above linear polarization measures the total resistance of the system, ($R_s+R_p$). Electrochemical impedance spectroscopy (EIS) experiments were performed with a Schlumberger Solartron Model 1255 Frequency Response Analyzer (FRA) through an EG&G Princeton Applied Research Models 273 Potentiostat. A ±10 mV sinusoidal AC signal of different frequencies ranging from 10 KHz to 1 mHz, or lower, was applied to the working electrode to determine the solution resistance as the high frequency limit and the total resistance as the low frequency limit. Since EIS provides the response of the system over a wide frequency range we feel it is the best method available to access the accuracy of the present invention for the determination of $R_s$ and $R_p$.

Tables 2–4 below show the results obtained with the steel wire corrosion probe at various conductivities in deaerated deionized water at room temperature using linear polarization (LP), electrochemical impedance spectroscopy (EIS), and the corrosion monitor with the peak detector.

TABLE 2

Deaerated Deionized Water; Conductivity = 0.72 μs/cm (units: ohms cm$^2$)

| | | Corrosion Monitor (Steel Wire Corrosion Probe) | | | |
|---|---|---|---|---|---|
| LP | EIS | Test #1 | Test #2 | Test #3 | Average |
| | $R_s$ = 151.5K | $R_s$ = 0.0K | 0.0K | 0.0K | 0.0K |
| | $R_p$ = 16.5K | $R_p$ = 155.9K | 157.5K | 157.6K | 157.0K |
| $R_s + R_p$ = 157.5K | $R_s + R_p$ = 168K | $R_s + R_p$ = 155.9K | 157.5K | 157.6K | 157.0K |

TABLE 3

Deaerated Deionized Water; Conductivity = 3.94 μs/cm (units: ohms cm$^2$)

| | | Corrosion Monitor (Steel Wire Corrosion Probe) | | | |
|---|---|---|---|---|---|
| LP | EIS | Test #1 | Test #2 | Test #3 | Average |
| | $R_s$ = 18K | $R_s$ = 17.2K | 16.7K | 17.5K | 17.1K |
| | $R_p$ = 14.4K | Rp = 16.6K | 16.8K | 16.8K | 16.7K |
| $R_s + R_p$ = 31.8K | $R_s + R_p$ = 32.4K | $R_s + R_p$ = 33.8K | 33.5K | 34.3K | 33.8K |

TABLE 4

Deaerated Deionized Water; Conductivity = 4.7 μs/cm (units: ohms cm$^2$)

| | | Corrosion Monitor (Steel Wire Corrosion Probe) | | | |
|---|---|---|---|---|---|
| LP | EIS | Test #1 | Test #2 | Test #3 | Average |
| | $R_s$ = 18.3K | Rs = 17.9K | 18.7K | 16.9K | 17.8K |
| | $R_p$ = 13.5K | $R_p$ = 15.3K | 14.0K | 15.8K | 15.0K |
| $R_s + R_p$ = 30.9K | $R_s + R_p$ = 31.8K | $R_s + R_p$ = 33.2K | 32.7K | 32.7K | 32.8K |

Good agreement was observed between LP, EIS, and corrosion monitor for measuring the total resistance ($R_s + R_p$). At the lowest conductivity (0.72 μS/cm), the corrosion monitor could not measure the solution resistance causing a significant error in $R_p$ (Table 2). This problem was noticed previously in Table 2 when using a dummy cell at the highest solution resistance ($R_s$=56K ohms and $R_p$=479K ohms). This can be attributed to the small excitation step (2 mV) used in the potential signal for measuring the solution resistance and/or the resolution limitations of the A/D and D/A cards.

The corrosion monitor displayed excellent accuracy in solutions of higher conductivity (3.94 μS/cm Table 3; 4.7 μS/cm Table 4). Conductivity was adjusted by the addition of trace amounts of NaClO$_4$ to the deionized test water. Good agreement was observed between LP, EIS, and the corrosion monitor for measuring ($R_s + R_p$). The values of $R_s$ and $R_p$ measured with the corrosion monitor were also in good agreement with that measured with EIS (Tables 3 and 4).

3. Improvement of the Corrosion Monitor

To improve the performance of the corrosion monitor, the potential signal was changed to a single step excitation with an amplitude of ±10 mV as that shown in FIG. 2 with $E_a$=±10 mV. The software for driving the corrosion monitor was also modified to automatically select the current range to obtain the best possible resolution of the A/D and D/A cards. The modified corrosion monitor was tested with dummy cells consisting of different resistors and a 100 μF capacitor (FIG. 1) to demonstrate its improved operating range. The results are summarized in Tables 5 to 9.

TABLE 5

DUMMY CELL EXPERIMENTS (Units: ohms); $R_s$ = 0.1K

| Dummy Cell C = 100 μF | Test #1 | Test #2 | Test #3 | Test #4 | Test #5 | Average |
|---|---|---|---|---|---|---|
| $R_s$ = 0.1K | 0.104K | 0.104K | 0.104K | — | — | 0.104K |
| $R_p$ = 0.1K | 0.096K | 0.093K | 0.093K | — | — | 0.094K |
| $R_s$ = 0.1K | 0.101K | 0.000K | 0.102K | 0.101K | — | 0.076K |
| $R_p$ = 1.0K | 1.00K | 1.00K | 1.01K | 1.00K | — | 1.00K |
| $R_s$ = 0.1K | 0.099K | 0.098K | 0.099K | — | — | 0.099K |
| $R_p$ = 10K | 10.3K | 10.3K | 10.2K | — | — | 10.27K |
| $R_s$ = 0.1K | 0.102K | 0.105K | 0.099K | — | — | 0.102K |
| $R_p$ = 100K | 98.3K | 94.5K | 97.3K | — | — | 96.7K |
| $R_s$ = 0.1K | 0.099K | 0.104K | 0.100K | — | — | 0.101K |
| $R_p$ = 220K | 288K | 213K | 105K | — | — | 202K |
| $R_s$ = 0.1K | 0.101K | 0.101K | 0.103K | 0.103K | — | 0.102K |
| $R_p$ = 479K | 436K | 694K | 40.6K | 214.K | — | 346.2K |

TABLE 6

DUMMY CELL EXPERIMENTS (Units: ohms); $R_s$ = 1.0K

| Dummy Cell C = 100 μF | Test #1 | Test #2 | Test #3 | Test #4 | Test #5 | Average |
|---|---|---|---|---|---|---|
| $R_s$ = 1.0K | 1.09K | 1.10K | 1.11K | 0.00K | 1.16K | 0.892K |
| $R_p$ = 1.0K | 0.872K | 0.880K | 0.888K | 1.94K | 0.844K | 1.085K |
| $R_s$ = 1.0K | 1.02K | 1.04K | 1.05K | 1.05K | 1.05K | 1.04K |
| $R_p$ = 10K | 9.94K | 9.96K | 9.90K | 9.89K | 9.89K | 9.92K |
| $R_s$ = 1.0K | 1.03K | 1.03K | 1.04K | 0.00K | 1.02K | 0.824K |
| $R_p$ = 100K | 98.0K | 102K | 98.6K | 99.7K | 97.3K | 99.12K |
| $R_s$ = 1.0K | 1.02K | 1.83K | 1.02K | 1.02K | 1.02K | 1.18K |
| $R_p$ = 200K | 196K | 199K | 186K | 218K | 193K | 198.4K |
| $R_s$ = 1.0K | 1.03K | 1.01K | 1.01K | 0.996K | 0.991K | 1.01K |
| $R_p$ = 500K | 540K | 561K | 566K | 561K | 553K | 556K |

TABLE 7

DUMMY CELL EXPERIMENTS (Units: ohms); $R_s = 10K$

| Dummy Cell C = 100 μF | Test #1 | Test #2 | Test #3 | Test #4 | Test #5 | Average |
|---|---|---|---|---|---|---|
| $R_s$ = 10K   | 9.94K | 9.93K | 10.1K | —     | —     | 9.9K    |
| $R_p$ = 1.0K  | 1.29K | 1.28K | 1.16K | —     | —     | 1.24K   |
| $R_s$ = 10K   | 10.0K | 9.83K | 10.1K | —     | —     | 9.98K   |
| $R_p$ = 56K   | 56.8K | 56.7K | 56.6K | —     | —     | 56.7K   |
| $R_s$ = 10K   | 10.1K | 10.2K | 9.94K | —     | —     | 10.08K  |
| $R_p$ = 100K  | 98.2K | 100K  | 102K  | —     | —     | 100.1K  |
| $R_2$ = 10K   | 9.96K | 9.96K | 9.96K | 9.80K | 9.91K | 9.92K   |
| $R_p$ = 220K  | 181K  | 187K  | 182K  | 221K  | 186K  | 191.4K  |
| $R_s$ = 10K   | 9.84K | 9.99K | 9.99K | 9.91K | —     | 9.93K   |
| $R_p$ = 479K  | 802K  | 327K  | 474K  | 682K  | —     | 571.3K  |
| $R_s$ = 10K   | 9.76K | 7.57K | 9.91K | 9.81K | 9.69K | 9.35K   |
| $R_p$ = 500K  | 527K  | 635K  | 463K  | 500K  | 505K  | 526K    |

TABLE 8

DUMMY CELL EXPERIMENTS (Units: ohms); $R_s = 50K$

| Dummy Cell C = 100 μF | Test #1 | Test #2 | Test #3 | Test #4 | Test #5 | Average |
|---|---|---|---|---|---|---|
| $R_s$ = 50K  | 49K    | 48.9K  | 51.1K | 49.4K | 51.5K | 49.98K |
| $R_p$ = 10K  | 8.84K  | 9.04K  | 7.85K | 9.59K | 7.46K | 8.56K  |
| $R_s$ = 50K  | 52.7K  | 53.7K  | 52.9K | 51.2K | 50.4K | 52.2K  |
| $R_p$ = 50K  | 48.4K  | 48.8K  | 48.2K | 49.8K | 50.8K | 49.2K  |
| $R_s$ = 50K  | 51.5K  | 49.5K  | 51.1K | 51.5K | 49.4K | 50.6K  |
| $R_p$ = 100K | 99.5K  | 109K   | 109K  | 109K  | 110K  | 107.3K |
| $R_s$ = 50K  | 49.2K  | 48.5K  | 51.8K | 50.5K | 48.2K | 49.64K |
| $R_p$ = 200K | 202K   | 198K   | 177K  | 190K  | 196K  | 192.6K |

TABLE 9

DUMMY CELL EXPERIMENTS (Units: ohms); $R_s = 100K$

| Dummy Cell C = 100 μF | Test #1 | Test #2 | Test #3 | Test #4 | Test #5 | Average |
|---|---|---|---|---|---|---|
| $R_s$ = 100K | 104K   | 101K   | 100K  | 110K  | 103K  | 103.6K |
| $R_p$ = 10K  | 10.2K  | 13.4K  | 13.7K | 4.41K | 10.2K | 10.38K |
| $R_s$ = 100K | 102K   | 105K   | 109K  | 104K  | 99.9K | 104K   |
| $R_p$ = 22K  | 20.4K  | 17.6K  | 13.0K | 18.7K | 22.8K | 18.5K  |
| $R_s$ = 100K | 100K   | 107K   | 99.1K | 104K  | 107K  | 103.4K |
| $R_p$ = 56K  | 67.1K  | 58.7K  | 67.1K | 62.9K | 59.8K | 63.1K  |
| $R_s$ = 100K | 104K   | 103K   | 101K  | 105K  | 104K  | 103.4K |
| $R_p$ = 100K | 94.3K  | 96.9K  | 96.6K | 91.3K | 93.8K | 94.6K  |
| $R_s$ = 100K | 108K   | 111K   | 104K  | 102K  | 103K  | 105.6K |
| $R_p$ = 220K | 265K   | 261K   | 270K  | 265K  | 269K  | 266K   |
| $R_s$ = 100K | 100K   | 99.8K  | 121K  | 101K  | 103K  | 105K   |
| $R_p$ = 479K | 467K   | 471K   | 414K  | 407K  | 426K  | 437K   |
| $R_s$ = 100K | 97.3K  | 101K   | 102K  | 111K  | 106K  | 103.5K |
| $R_p$ = 500K | 469K   | 479K   | 486K  | 478K  | 478K  | 478K   |

Good performance was observed with the modified corrosion monitor at various values of $R_s$ and $R_p$. The range of $R_s$ tested was from 0.1K to 100K representing a variety of solution resistance typical of industrial environments including the boiler condensate, boiler feed water, cooling water environments, and other aqueous and non-aqueous solutions. We believe that the operating range of the corrosion monitor with the peak detector can further be improved by enhancing the resolution of the A/D and D/A cards and by increasing the amplitude of the potential step from ±10 mV to ±20 mV or ±30 mV. However, we still prefer to use a ±10 mV excitation whenever possible to minimize the perturbation of the corroding interface and prevent any irreversible changes in the electrode surface. Increasing the amplitude of the potential step should also improve the signal/noise ratio especially under plant conditions.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim as our invention:

1. A method for determining the solution resistance at an interface of a metal surface wherein the metal surface is a corroding electrode of an electrochemical cell comprising the steps of:
   a) applying a small amplitude potential step signal generated by a digital-to-analog converter to the metal surface which simulates industrial water system piping;
   b) monitoring the response current generated by an electrochemical cell as a result of signal application in step (a) and converting the response current to a voltage signal;
   c) providing a peak detector;
   d) applying the voltage signal derived from the response current to the peak detector;
   e) determining the peak of the response; and
   f) ascertaining the solution resistance from the peak by dividing the voltage applied in step (a) by the peak of the response determined in step (e).

2. The method of claim 1 wherein the solution is selected from the group consisting of boiler feed water, steam condensate, or other aqueous or non-aqueous solutions having a low conductivity.

3. The method of claim 1 wherein the solution is cooling water.

4. The method of claim 1 wherein the solution is highly corrosive.

5. The method of claim 1 wherein the value of the solution resistance is not negligible when compared to the polarization resistance such that total resistance is not substantially equal to polarization resistance.

6. A method for determining corrosion rate of a metal surface in a solution comprising the steps of:
   a) determining the solution resistance by
      i) applying a small amplitude potential step signal generated by a digital-to-analog converter to the metal surface which simulates industrial water system piping;
      ii) monitoring the response current generated by an electrochemical cell as a result of signal application in step (i) and converting the response current to a voltage signal;
      iii) providing a peak detector;
      iv) applying the voltage signal derived from the response current to the peak detector;
      v) determining the peak of the response; and
      vi) ascertaining the solution resistance from the peak by dividing the voltage applied in step (i) by the peak of the response determined in step (v) and then;
   b) determining the total resistance of the metal surface in the solution from the steady state value of response current, obtained at a selected time interval after applying the response to the peak detector for determining the peak, or by the linear polarization technique;

c) determining polarization resistance by subtracting the solution resistance of step (a) from the total resistance of step (b); and, d) calculating the corrosion rate of the metal surface from the polarization resistance.

7. The method of claim 6 wherein the solution is selected from the group consisting of boiler feed water, steam condensate, or other aqueous or non-aqueous solutions having a low conductivity.

8. The method of claim 6 wherein the solution is cooling water.

9. The method of claim 6 wherein the solution is highly corrosive.

10. The method of claim 6 wherein the value of solution resistance is not neglible when compared to the polarization resistance.

* * * * *

UNITED STATES PATENT AND TRADEMARK OFFICE
Certificate

Patent No. 5,448,178                                              Patented: September 5, 1995

On petition requesting issuance of a certificate for correction of inventorship pursuant to 35 U.S.C. 256, it has been found that the above-identified patent, through error and without deceptive intent, improperly sets forth the inventorship.

Accordingly, it is hereby certified that the correct inventorship of this patent is: Tzu-Yu Chen, Naperville, IL; Frank Fun-Yuee Lu, Naperville, IL; Martin R. Godfrey, Elburn, IL; and Jerry Haney, Sunnyvale, CA.

Signed and Sealed this Twenty-Ninth Day of February, 2000.

JOSIE A. BALLATO
*Supervisory Patent Examiner*
                                                                             Art Unit 2858